United States Patent [19]

McRae

[11] Patent Number: Plant 6,376

[45] Date of Patent: Nov. 8, 1988

[54] LILY PLANT NAMED 'ROUGE PIXIE'

[75] Inventor: Edward A. McRae, Boring, Oreg.

[73] Assignee: Melridge, Inc., Aurora, Oreg.

[21] Appl. No.: 931,433

[22] Filed: Nov. 17, 1986

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of hybrid Asiatic lily plant having very short stems bearing large clusters of medium sized, upright flowers particularly distinguished by their vivid orange-red coloration and generally inconspicuous spots, excellent flower form, long persistence and an abundance of foliage, making this plant especially suitable as a pot plant variety. The color pattern of this new plant and its silhouette are completely new in the upright Asiatic divisions of lilies suited for forcing and mass commercial cultivation. The plant is an excellent garden plant highly resistant to diseases and showing high tolerance of virus and its bulbs may be precooled and forced throughout the year for pot plant production.

1 Drawing Sheet

BACKGROUND OF THE INVENTION

My new variety of lily plant originated as a seedling selected from a group of seedlings planted by me at Sandy, Oreg., and resulting from my using a very short, cream flowered clonal selection from the 'Pastel Hybrids' strain as the seed parent and, as the pollen parent, a red-orange flowered seedling from 'Connecticut Lemonglow'×'Red Carpet'. The object of this crossing was the production of lilies in shades of orange and red well suited to forcing for pot plant production out of season; and this particular seedling was selected by me for propagation because it appeared to possess characteristics of the kind that I was seeking such as medium size, vivid orange-red coloration and minimum spotting, a color pattern unique in this type Asiatic lily. This selected plant was asexually reproduced by me at Sandy, Oreg., with results so pleasing that propagation was continued under my direction through several successive generations by bulb scale propagation and natural propagation from bulblets. This work demonstrated clearly that the novel and desirable characteristics of this plant would hold true from generation to generation and appeared to be firmly fixed.

It was found that the stature of this new variety remained short and is not overly susceptible to bud abortion when forced into flower out of season as a pot plant and, in addition, it was found that the clone possesses to a high degree the desirable characteristics of hybrid vigor, great hardiness and disease resistance, as well as being a vigorous and good grower and propagator.

It was also found that this new plant is well suited to forcing out of season when the bulbs are dug at the appropriate time and properly precooled; October-dug bulbs, properly precooled and potted in January, will flower under glass in western Oregon, with no supplementary lighting and at moderate greenhouse temperatures, in an average of 60 to 70 days.

DESCRIPTION OF THE DRAWING

My new variety of lily plant is illustrated by the accompanying drawing, which shows the open bloom in full color and illustrates the flower form, as well as the novel and distinctive orange-red characteristics, the colors shown being as true to those specified herein as is possible to obtain by conventional photographic procedures.

DESCRIPTION OF THE NEW VARIETY

The following is a detailed description of my new variety of Asiatic hybrid lily with nomenclature according to The International Lily Register of The Royal Horticultural Society of London, England (Second Edition, 1969), and the color designations are according to The R.H.S. Colour Chart (1966).

THE PLANT

Origin: Seedling.

Parentage:

- *Seed parent.*—An unnamed and unpatented, short, cream colored 'Pastel Hybrid' clonal lily.
- *Pollen parent.*—An unnamed and unpatented red-orange flowered selection from 'Connecticut Lemonglow'×'Red Carpet'.

Classification:

- *Horticultural.*—Upright Asiatic Hybrid Lily, Division I-A of the Horticultural Classification of Lilies by The Royal Horticultural Society of London, England.
- *Commercial.*—Hybrid Lily Cultivar.

Form: Single stem, erect and stately.

Height: About 30 to 40 cm. for stems produced by glasshouse forcing of bulbs of about 12 to 18 cm. in circumference with adequate light levels.

Growth: Vigorous and upright.

Foliage:

- *Quantity.*—Abundant.
- *Leaf size.*—About 8 to 12 cm. long and about 1 cm. wide, in average.
- *Leaf shape.*—Lanceolate with acute tip.
- *Texture.*—Leathery.
- *Appearance.*—Glossy.
- *Color.*—Medium green, somewhat lighter on the bottom side.

Bulbs:

- *Size.*—Various, ranging to about 25 cm. in circumference in commercial use.
- *Color.*—White.

THE BUD

Form: Long, ovoid and obtuse.

Size: About 8 to 9 cm. long and about 5 cm. in circumference just prior to opening.

Opening rate: The bud opens slowly, in about one hour in response to morning light.

Color: Medium red-orange with flush of green along the midribs and at the tip prior to opening and as the tepals begin to unfurl.

Peduncle:

*Length.*—Averages about 4 to 6 cm., but may be longer if light levels are too low or if bulbs have been improperly stored prior to forcing.

*Color.*—Medium green.

THE FLOWER

Blooming habit: Once annually, blooming profusely in midseason for Asiatic lilies.

Size: Medium, averaging about 12 to 15 cm. in diameter.

Borne: Racemose on a single stem producing 9 to 12 buds from a bulb of about 12 to 16 cm. in circumference.

Shape: Cup-shaped when first opening, flattening as the tepals recurve during the second day.

Tepalage:

*Number.*—Six.

*Arrangement.*—Hexagonal and imbricated.

*Shape.*—Ovate with entire margins and acute tip.

*Appearance.*—Shiny.

*Color.*—Orange red, 30B to 28A, with a flush of 33A which is about 1 to 2 mm. wide parallel to the nectaries. The nectaries are deep orange overlaid with white pubescence.

*Color changes.*—The flower color may become slightly less red and more orange as it ages, depending upon light levels; usually there is only a slight change if the light levels are adequate for cut flower and pot plant maintenance.

Appearance: Shiny.

Pedicel:

*Length.*—About 4 to 8 cm.

*Form.*—Sturdy and ascending up to 60° from the horizontal.

*Color.*—Medium to dark green.

Persistence: The tepals stay on the stem for about 3 weeks.

Fragrance: None.

Disease resistance: The flower and plant are resistance to disease; in particular, they are resistant to Botrytis blight and to Fusarium bulb rot.

Lasting quality: The flower is long lasting.

THE REPRODUCTIVE ORGANS

Stamens:

*Number.*—Six.

*Arrangement.*—Typical of the genus Lilium.

*Anthers (dehisced) and pollen.*—Greyed orange, 169A and 171A.

*Filaments.*—Length: About 5 cm. Color: Soft red, 47D.

Pistils:

*Number.*—One.

*Style.*—Length: About 5 cm.

*Stigma.*—Size: Medium. Color: Soft orange.

Ovary: Typical of genus Lilium.

THE FRUIT

Fertility: The fruit is fertile.

Shape: Ovoid.

Color at maturity. Soft brown, sometimes overlaid with soft plum.

This new variety of lily most closely resembles 'Red Carpet' but is distinguished by having a lighter and less brown color, a more compact inflorescence with shorter pedicels and a higher bud count; the plant is shorter in height with shorter leaves and it is also more reliable and uniform in its forcing performance than 'Red Carpet'; also, it can be forced into flower much more rapidly than 'Red Carpet' and has green stems and pedicels unlike the black stems of 'Red Carpet'.

I claim:

1. A new and distinct variety of Asiatic hybrid lily, substantially as herein shown and described, particularly characterized by its orange-red flowers, the excellence of its flower form and by its short height and abundant foliage providing an upright flowering silhouette ideal for a pot plant.

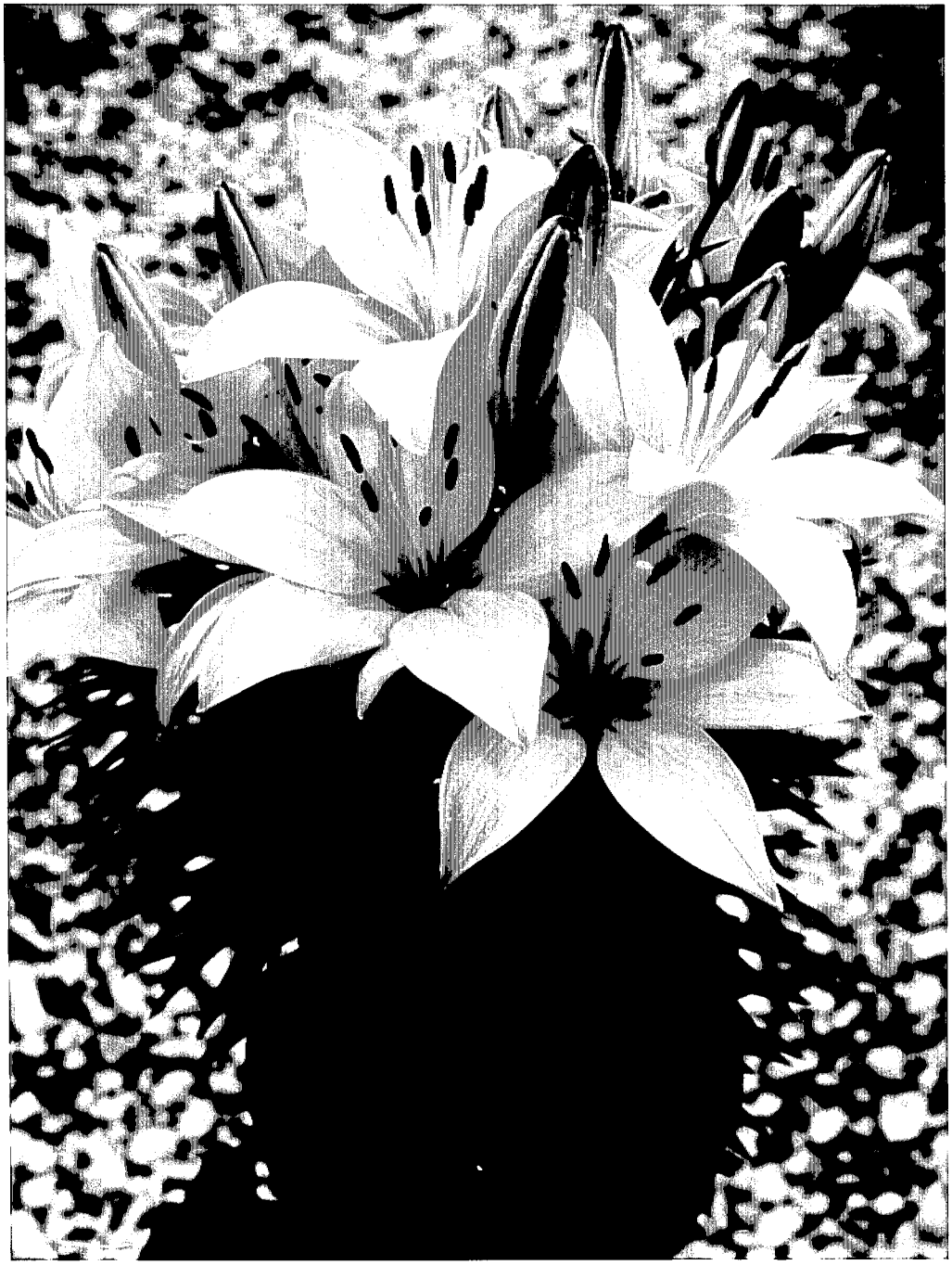

* * * * *